United States Patent [19]

Hauschild et al.

[11] Patent Number: 5,048,510
[45] Date of Patent: * Sep. 17, 1991

[54] INFLATABLE PENILE PROSTHESIS WITH SATELLITE RESERVOIR

[75] Inventors: Sidney F. Hauschild, Hendricks; John C. Hill, Minnetonka; Dezso K. Levius, Bloomington, all of Minn.

[73] Assignee: American Medical Systems, Inc., Minnetonka, Minn.

[*] Notice: The portion of the term of this patent subsequent to Jan. 23, 2007 has been disclaimed.

[21] Appl. No.: 237,926

[22] Filed: Aug. 29, 1988

[51] Int. Cl.⁵ .............................................. A61F 2/26
[52] U.S. Cl. ...................................................... 128/79
[58] Field of Search ........................................... 128/79

[56] References Cited

U.S. PATENT DOCUMENTS

| | | | |
|---|---|---|---|
| 3,954,102 | 5/1976 | Buuck | 128/79 |
| 4,267,829 | 5/1981 | Burton et al. | 128/79 |
| 4,590,927 | 5/1986 | Porter et. al. | 128/79 |
| 4,671,261 | 6/1987 | Fischell | 128/79 |
| 4,726,360 | 2/1988 | Trick et al. | 128/79 |
| 4,782,826 | 11/1988 | Fogarty | 128/79 |

*Primary Examiner*—Cary E. Stone
*Attorney, Agent, or Firm*—Peter C. Richardson; Lawrence C. Akers; Gezina Holtrust

[57] ABSTRACT

An implantable penile prosthesis comprises a tubular body for implantation in a patient's penis and a fluid reservoir for implantation in a patient's body outside the penis. The tubular body and reservoir are in fluid communication with each other. The tubular body comprises a tubular chamber which is inflatable from a flaccid to an erect state when filled substantially to capacity. Fluid flow to and from the chamber is by way of a manually actuatable valve system. The valve system moves between an open position allowing for change from the erect state to the flaccid state, and a closed position allowing for change from the flaccid state to the erect state.

7 Claims, 6 Drawing Sheets

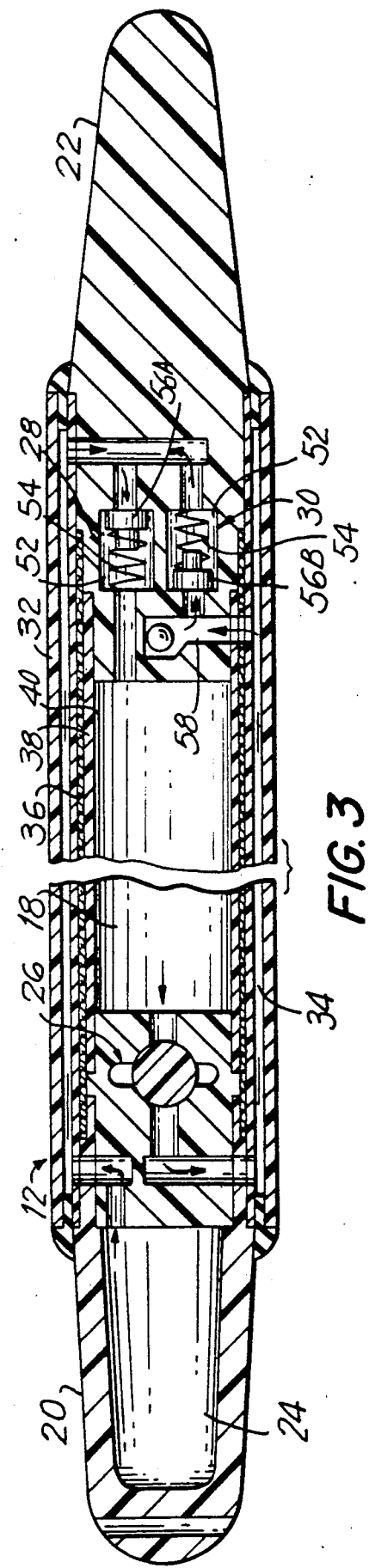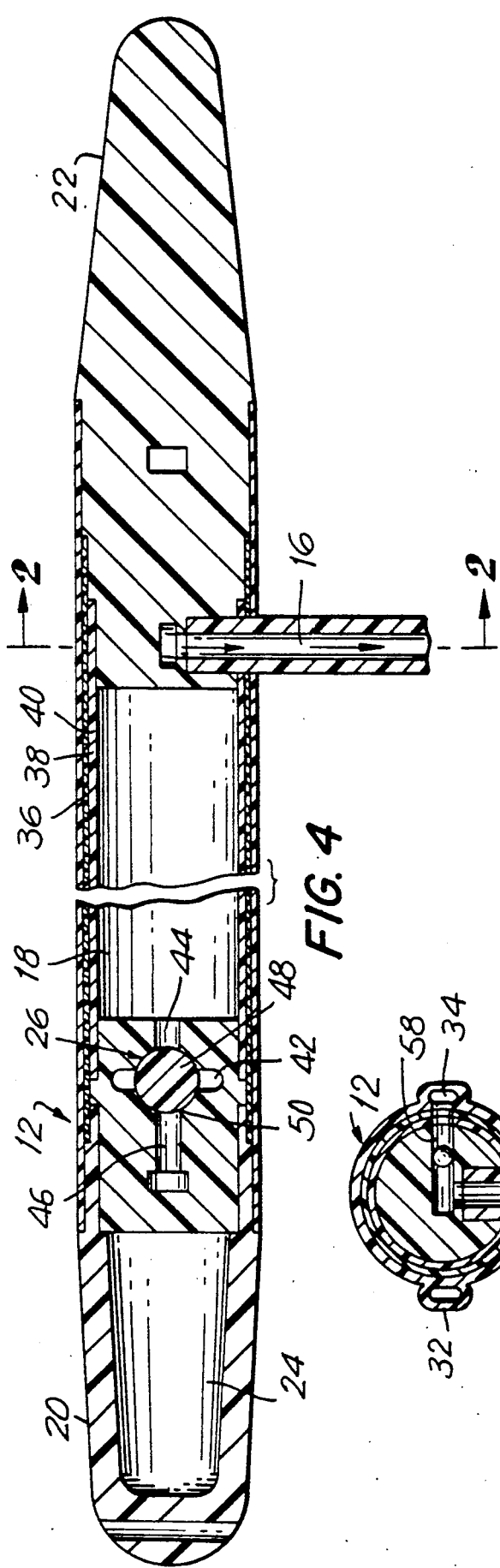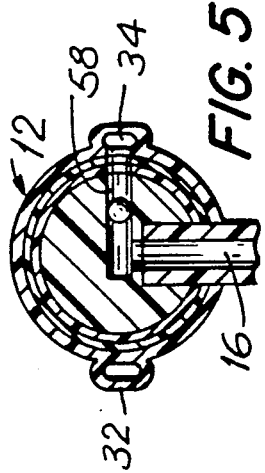

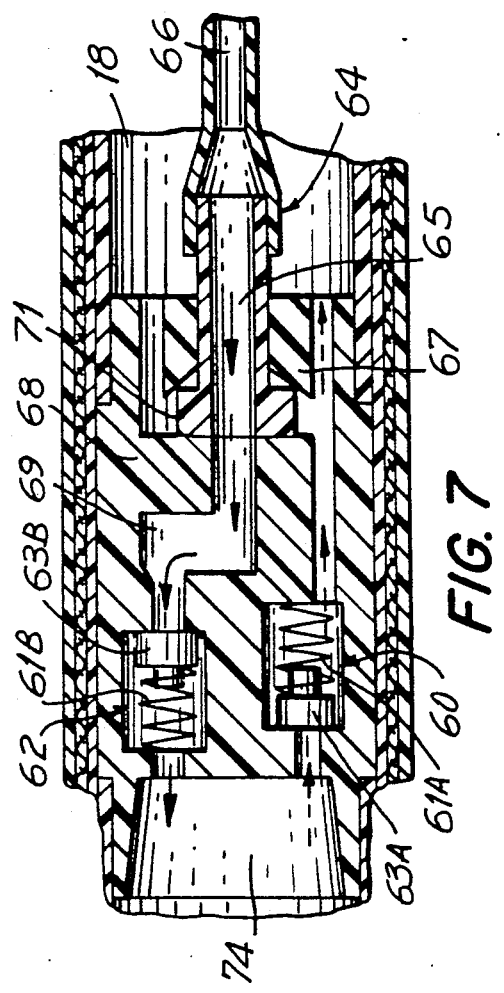
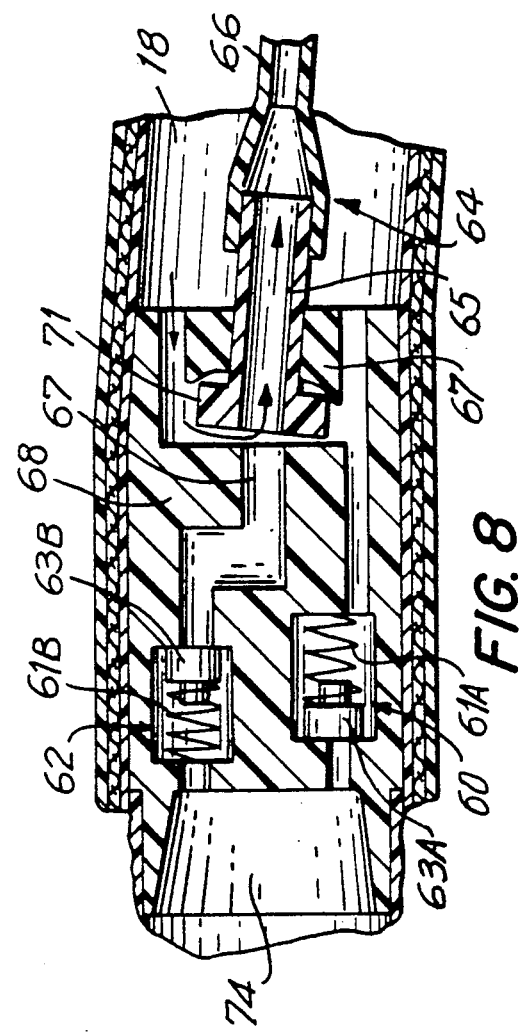

INFLATABLE PENILE PROSTHESIS WITH SATELLITE RESERVOIR

BACKGROUND OF THE INVENTION

This invention relates to an implantable penile prosthesis comprising a tubular body implanted in the penis for inflation to an erect state when said body is substantially filled to capacity with a fluid from a satellite reservoir implanted in a patient's body outside the penis.

Inflatable penile devices described in the prior art generally include a tubular body for implantation in one, or usually both, of the corpus cavernosum of a patient's penis. The user produces an erection by pumping fluid to inflate the tubular body. Deflation is generally attained by manipulation of a valve system. The fluid inflatable devices require relatively large amounts of fluid to attain an erection which is sufficient to withstand the pressures and stresses during sexual intercourse. Fluid reservoirs have been implanted extraneous to the penis to accomodate the fluid requirements. U.S. Pat. No. 3,954,102 describes one such system requiring rather extensive surgery. Less invasive surgery is required with the device of U.S. Pat. No. 4,267,829 having a satellite reservoir implanted in the scrotum of a patient. Deflation of this device to the flaccid state is by manipulation of a pull valve, which is also located in the scrotum and therefore difficult to reach. U.S. Pat. No. 4,590,927 describes a self-contained device requiring limited surgery and simplified manipulation of the penis. However, the limited amount of fluid available for inflation of this self-contained device limits the usefullness thereof.

SUMMARY OF THE INVENTION

According to the invention, an implantable penile prosthesis is provided comprising (1) a generally tubular body implantable within one or both corpus cavernosa of the penis to simulate a natural erection; and (2) a fluid reservoir implantable in a patient's body in fluid communication with said tubular body; said tubular body comprising: (a) a generally tubular chamber inflatable from a flaccid to an erect state when filled with a fluid substantially to capacity and deflatable from the erect state to the flaccid state when substantially free of fluid; and (b) a manually actuatable valve system for controlling fluid flow between said tubular chamber and said fluid reservoir, said valve system movable between at least two different positions, a first open position allowing for change from the erect state to the flaccid state, and a second closed position allowing for change from the flaccid state to the erect state.

The fluid reservoir implantable in a patient's body, e.g. the scrotum, provides sufficient fluid to inflate the tubular chamber to a desirable extent and allows for sufficient drainage of the tubular chamber to reach a desirable flaccid state. The location of the manually actuatable valve in the tubular body in the penis facilitates manipulation by the user.

In a preferred embodiment of the invention, the valve system is operatively connected to said distal section and is movable from the first open position to the second closed position by manual compression of the distal section of the tubular body. Such manual compression may activate a pump located in the distal section.

In one embodiment of the invention, the valve system comprises a means for controlling fluid flow from the fluid reservoir to the tubular chamber to attain the erect state, and a first valve for controlling fluid flow in the other direction, from the tubular chamber to the fluid reservoir, to attain the flaccid state. Specifically, the above means comprises a pump, preferably located in the distal section, and a second valve, preferably located in the proximal section, the second valve being in fluid communication with the pump to allow an irreversible fluid flow from the fluid reservoir to the tubular chamber on compressing the pump.

In a preferred embodiment, the valve system is movable from the second closed position to the first open position by bending of the penis in any direction including a direction towards the patient's body.

BRIEF DESCRIPTION OF THE DRAWINGS

FIG. 3 is a cross-sectional view taken generally along line 1—1 of FIG. 2 showing a valve system according to the invention.

FIG. 4 is a cross-sectional view taken generally along line 1—1 of FIG. 2 through the tube leading to the fluid reservoir.

FIG. 5 is a cross-sectional view taken generally through Section 2—2 of FIG. 4.

FIG. 7 is a cross-sectional view of the valve system, including part of the pump, of FIG. 6 in the pumping position.

FIG. 8 is a cross-sectional view of the valve system, including part of the pump, of FIG. 6 in the release position.

DETAILED DESCRIPTION OF THE INVENTION

Like references are used for like parts throughout the description of the drawings.

Figure 1:
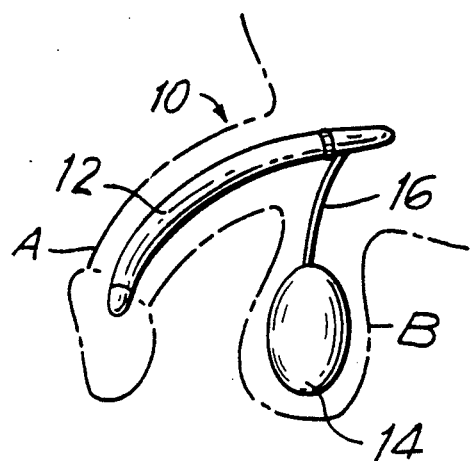
FIG. 1 is a side elevational view of the prosthesis of the invention in its fully implanted position, showing the penis in its flaccid state.
Figure 2:
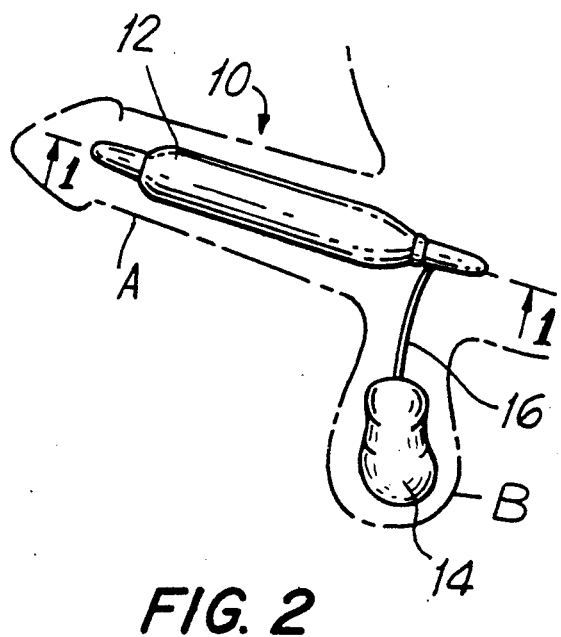
FIG. 2 is a side elevational view of the prosthesis of FIG. 1 showing the penis in its erect state.

FIG. 1 shows penile prosthesis 10 of the present invention including at least one generally tubular body 12, a fluid reservoir 14 and a reservoir tube 16 connecting tubular body 12 and fluid reservoir 14. Tubular body 12 is implanted in penis A and fluid reservoir 14 is implanted in scrotum B.

All of the components of prosthesis 10 including reservoir 14 and tube 16 are either composed of or covered by a biocompatible material such as silicone. Tubular body 12 is sized to be implanted within one corpus cavernosum of the penis. Usually, two tubular bodies 12 are implanted, one each in each corpus cavernosum, although one tubular body 12 may be implanted in either corpus cavernosum and still achieve useful results.

Referring to FIGS. 3 and 4, tubular body 12 includes tubular chamber 18, distal section 20 and proximal section 22. Proximal section 22 is usually positioned in the rear of the corpus cavernosum under the puboischiatic rami. Proximal section 22 is substantially rigid to support the penis during sexual intercourse. Proximal section 22 may be made of a number of materials, preferably silicone rubber. A conventional rear tip extender (not shown) may be provided to lengthen tubular body 12, if needed, to lessen the need for different prosthesis sizes.

Distal section 20 contains pump 24 which is manually actuatable for inflation of tubular chamber 18 which is located in series with respect to pump 24. Pump 24 is advantageously a hollow circular chamber. The pump supplies fluid pressure by lateral squeezing of distal section 20.

Tubular chamber 18 is positioned within tubular body 12 such that on implantation of tubular body 12, tubular chamber 18 lies approximately medially along the length of the corpus cavernosum.

The manually actuatable valve system for controlling fluid flow between tubular chamber 18 and the fluid reservoir comprises pump 24, pressure valve 28, suction valve 30 and ball deflate valve 26. The valve system in FIGS. 3 and 4 is in the second closed position. Pump 24 is in fluid communication with pressure valve 28 and suction valve 30, to allow an irreversible fluid flow from fluid reservoir 14 to tubular chamber 18 on compressing pump 24. Valves 28 and 30 are located in proximal section 22 in series with tubular chamber 18 along the length of tubular body 12. Pump 24 is in fluid communication with valves 28 and 30 through a first passageway 32 which is in fluid isolation from tubular chamber 18.

Tubular chamber 18 is in fluid communication with ball deflate valve 26 to allow for irreversible fluid flow from tubular chamber 18 through ball deflate valve 26 and second passageway 34, which is in fluid isolation from tubular chamber 18 and first passageway 32, to fluid reservoir 14.

As shown in FIGS. 3 and 4, first and second passageways 32 and 34 are in the form of a conduit extending axially along the length of tubular body 12 externally of tubular chamber 18. As a result, the device of the invention in one embodiment requires a trilumen tube, as apparent from FIG. 5. The diameters of the conduits are small relative to the diameter of the tubular chamber.

Referring to FIG. 5, second passageway 34 is in fluid communication with reservoir tube 16 through transfer passage 58 and allows fluid flow from second passageway 34 to fluid reservoir 14. As shown in FIG. 3, transfer passage 58 is also in fluid communication with suction valve 30 and allows fluid flow from reservoir 14, not shown, to suction valve 30.

The fluid of use in the prosthesis is a biocompatable fluid such as a physiological saline solution or a radioopaque fluid.

Tubular chamber 18 in FIGS. 3 and 4 has three different layers 36, 38 and 40. The outer layer 36 and the inner layer 40 are formed of any material which is elastic such as silicone elastomer. Materials which may be used for the three layers are disclosed in above U.S. Pat. No. 4,267,829. Particular reference is made to the vascular graft material of Dacro ® polyester fibers which is advantageous for middle layer 38. The three layers may be replaced by one layer having the desirable properties of elasticity, and imperviousness to liquids.

Ball deflate valve 26 is of the type described in above U.S. Pat. No. 4,590,927 as "bypass valve 50." The valve 26 includes a housing 42 having a proximal port 44 and a distal outlet 46. A ball 48 is normally seated on a seat 50 closing distal outlet 46. Other deflate valves may be used.

Pressure valve 28 and suction valve 30 are as described in above U.S. Pat. No. 4,590,927. Both valves include an enlarged housing 52, a coiled spring 54 and a valve member 56. The coiled spring 54 biases the valve member 56A of valve 28 proximally and the coiled spring 54 of valve 30 biases valve member 56B distally.

Figure 6:
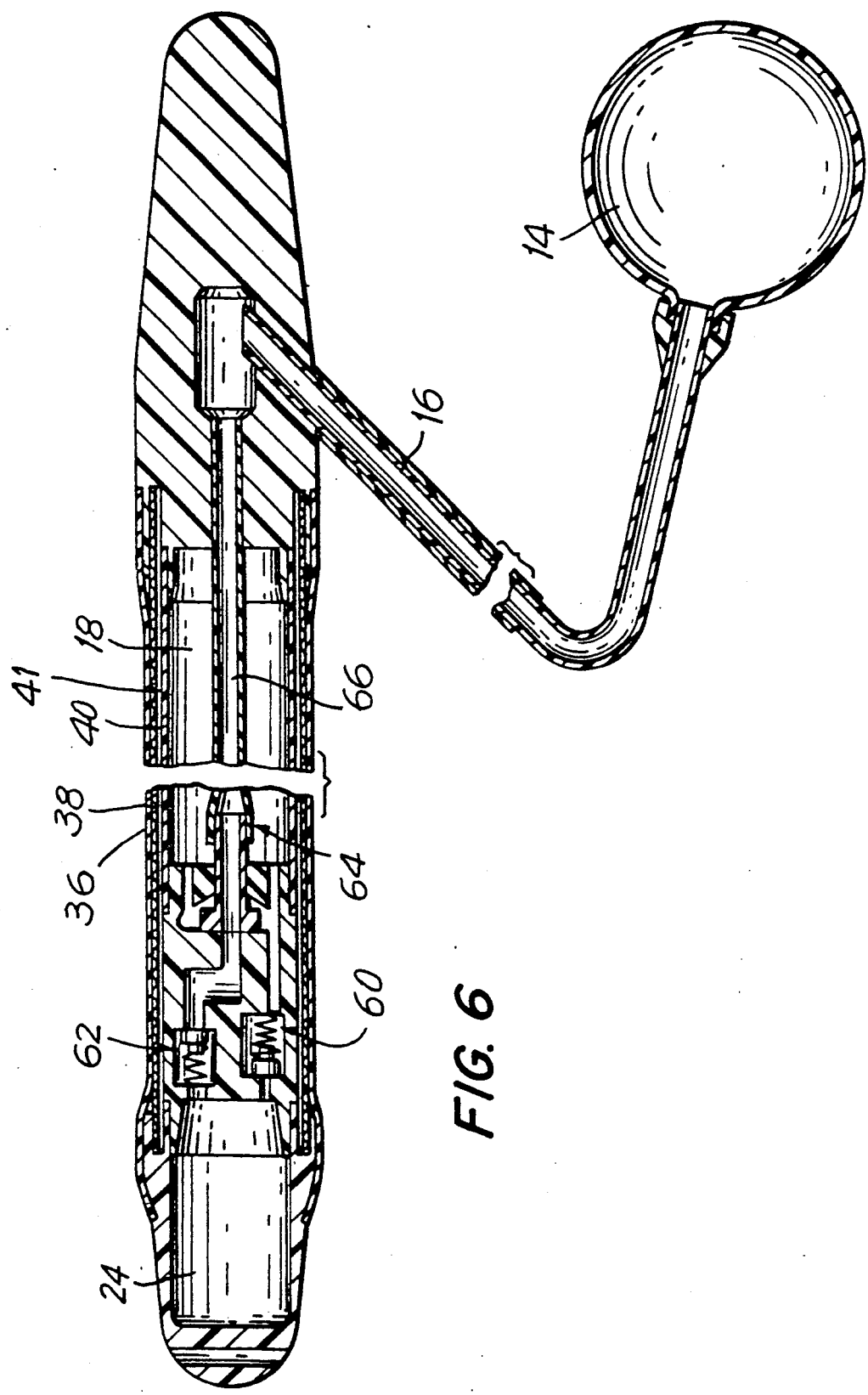
FIG. 6 is a cross-sectional view taken generally along line 1—1 of FIG. 2 showing a preferred valve system.

Referring to FIG. 6, the valve system comprises pump 24 in fluid communication with pressure check valve 60, low pressure check valve 62, and bend valve 64. Bend valve 64 is connected to reservoir 14 through central lumen 66 and tube 16.

Tubular chamber 18 in FIG. 6 has four different layers 36, 38, 40 and 41. The layers 36, 38, and 40 are as described above with reference to FIGS. 3 and 4 and may be replaced by one layer. Layer 41 is made of a wear-resistant material such as polytetrafluoroethylene.

FIGS. 7 and 8 show in more detail the valve system of FIG. 6 consisting of pump 24 (shown partly), valves 60, 62 and 64, and valve block 68. In FIG. 7, the valve system is in the second closed position or the pumping position. Bend valve 64 is sealed against valve block 68 so fluid can flow from the fluid reservoir through central lumen 66, bend valve 64 and low pressure check valve 62 into pump 24.

In FIG. 8, the valve system of FIG. 7 is in the first open position or the release position. Bend valve 64 is at an angle relative to valve block 68 allowing fluid to pass from tubular chamber 18 past valve block 68 and through valve 64, central lumen 66, and tube 16 (not shown) into the fluid reservoir.

High pressure check valve 60 and low pressure check valve 62 are similar to pressure and suction valves 28 and 30 by having a coiled spring 61A and 61B, respectively, which biases the valve members 63A and 63B, respectively.

Bend valve 64 includes a valve channel 65 which aligns with a valve block passage 67 in the closed position of FIG. 7. The alignment is broken in FIG. 8 when valve channel extension 71 compresses channel support block 69. Support block 69 is made of a material such as rubber which is compressed on bending of lumen 66 due to pressure exerted by valve channel extension 71.

Figure 9:
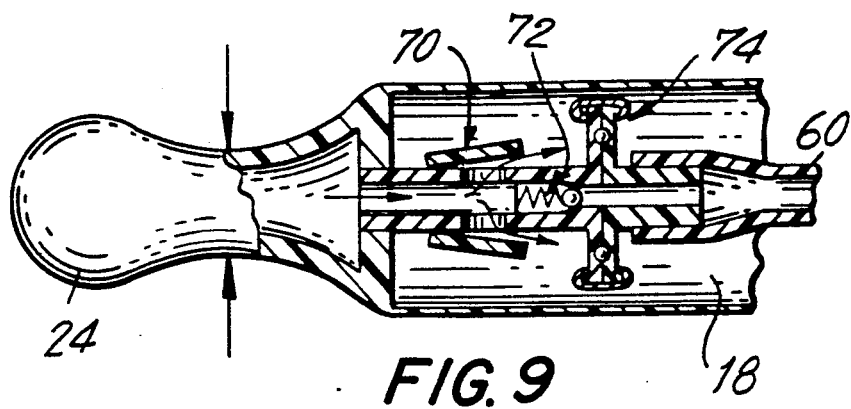
FIG. 9 is a cross-sectional view of a preferred valve system in the pressure phase of the pumping cycle.
Figure 10:
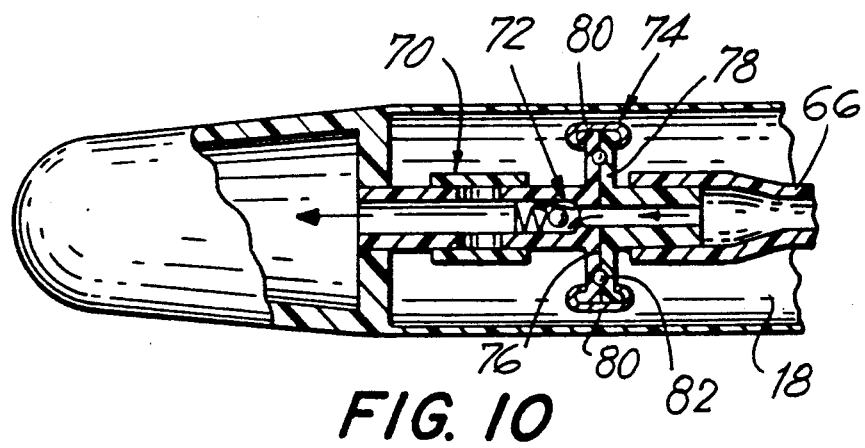
FIG. 10 is a cross-sectional view of the preferred valve system of FIG. 9 in the draw phase of the pumping cycle.
Figure 11:
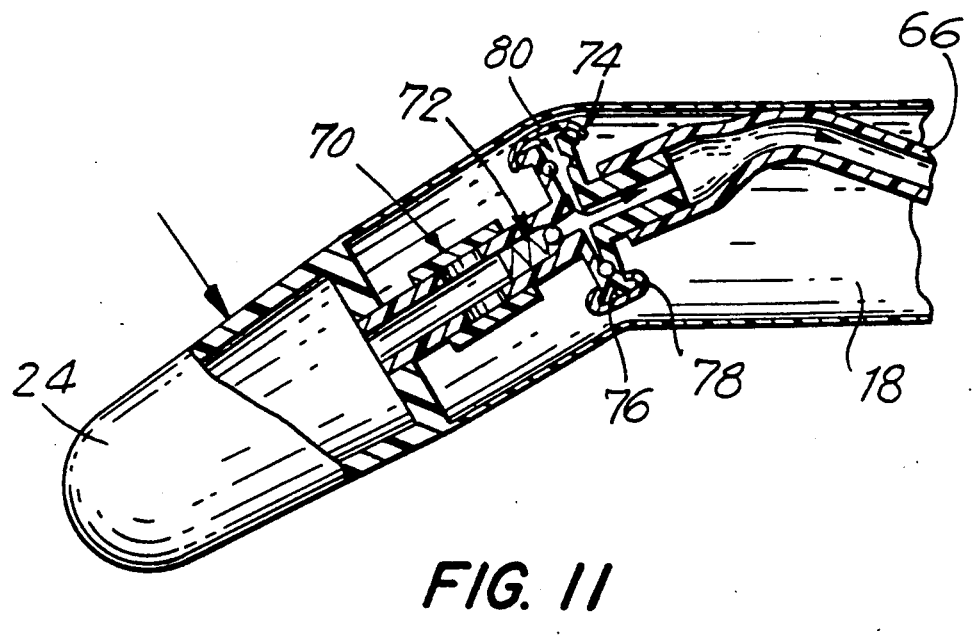
FIG. 11 is a cross-sectional view of the preferred valve system of FIG. 9 in the first open or release position.

The valve system of FIG. 6 may be replaced by the valve system of FIGS. 9 to 11 comprising the pump 24, the flap valve 70, the poppet valve 72, and the double flange valve 74. Referring to FIGS. 9 and 10, the valve system is in the second closed position. In FIG. 9, flap valve 70 is open allowing fluid flow from pump 24 into tubular chamber 18 whereas the poppet valve 72 and the double flange valve 74 are closed preventing fluid flow through lumen 66 back to the fluid reservoir 14 (not shown in FIGS. 9 to 11). In FIG. 10, flap valve 70 is closed, poppet valve 72 is open, and double flange valve 74 is closed so allowing fluid flow from the fluid reservoir to the pump 24 in the same way as shown in FIG. 6. In FIG. 11, the valve system is in the first open position or the release position. Spring retainer 80 is in a flexed position, double flange valve 74 is open, and poppet valve 72 and flap valve 70 are both closed allowing fluid flow from the tubular chamber 18 through open valve 74 and lumen 66 to the fluid reservoir 14.

The double flange valve 74 includes two flanges 76 and 78 which are held together by several spring retainers 80. O-ring seal 82 between flanges 76 and 78 seals the two flanges 76 and 78 to prevent fluid flow between the two flanges 76 and 78 when the valve 74 is closed.

Figure 12:
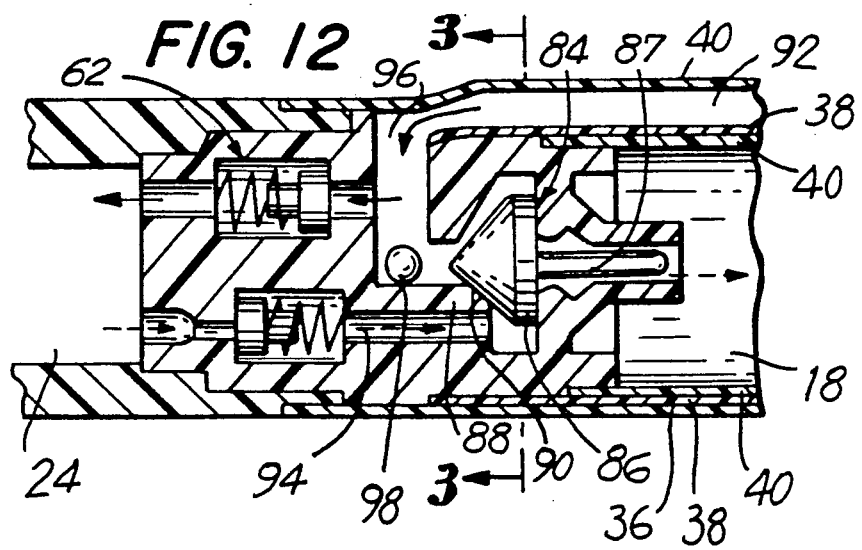
FIG. 12 is a cross-sectional view of a valve system according to the invention in the second closed position.
Figure 13:
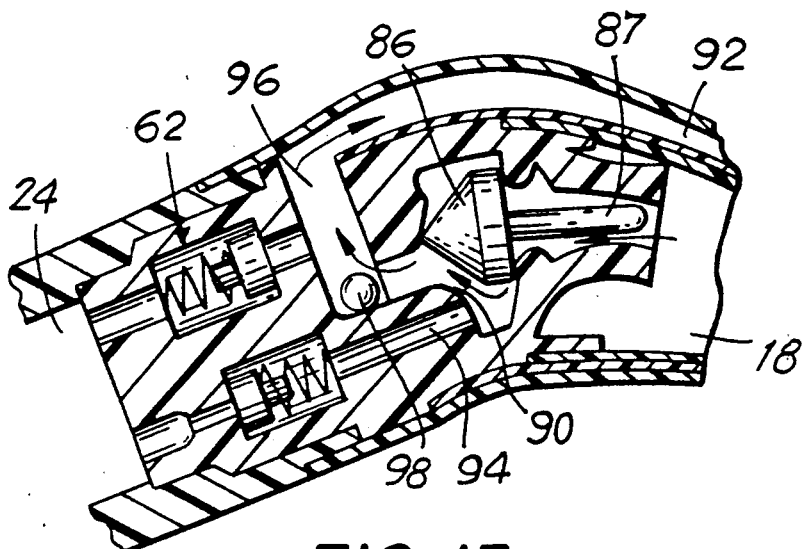
FIG. 13 is a cross-sectional view of the preferred valve system of FIG. 12 in the first open position.
Figure 14:
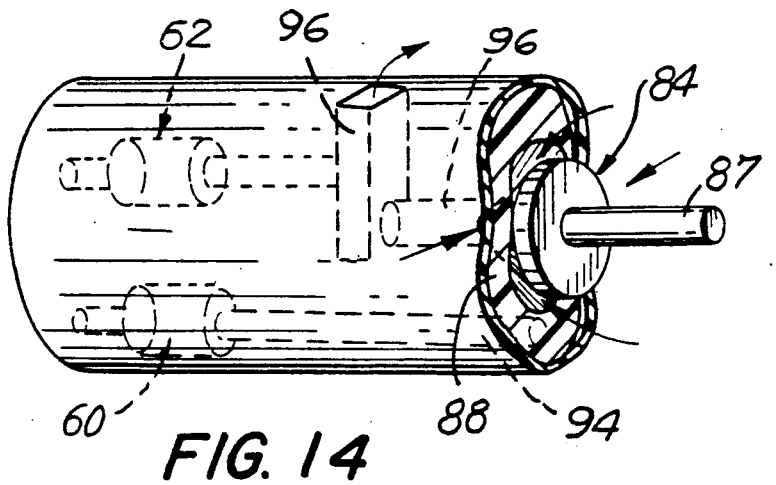
FIG. 14 is a perspective view of the preferred valve system of FIG. 12 in the first open position cut along line 3—3 of FIG. 12.

The penile prosthesis of FIG. 3 may be modified by replacing the ball deflate valve 26 by release valve 84 shown in FIGS. 12 to 14. The valve system of the so-modified penile prosthesis of FIG. 3 comprises pump 24, pressure valve 28, suction valve 30 and release valve 84. In FIG. 12, the valve system is in the second closed position or the pumping position. Cone 86 is sealed against valve block 88 so fluid can flow from the fluid reservoir 14 (not shown) through passageway 92 which is in fluid isolation from tubular chamber 18, as described above with reference to FIGS. 3 and 4. The fluid flows from passageway 92 through passageway 96 to pump 24. In FIG. 13, the valve system is in the first open position or the release position. When pressure is applied to valve stem 87, valve block 88 is deformed so fluid can flow from tubular chamber 18 past valve block 88 through passageways 96 and 92 (not shown) to fluid reservoir 14 (not shown), as indicated by arrows. In FIG. 14, the valve block 88 is squeezed such that the seat 90 against which the cone 86 rests is deformed around the cone 86. High pressure fluid from the tubular chamber 18 can then flow between cone 86 and valve block 88 through passageways 96 and 92 (not shown) to fluid reservoir 14 (not shown). On removal of squeeze or bend forces on the valve block, the seat 90 returns to its original shape, and the cone 86 creates a seal with the valve block 88.

The valve system of FIG. 6 may be replaced by the valve system of FIGS. 12 to 14 comprising the pump 24 (partly shown), high pressure check valve 60, low pressure check valve 62, and release valve 84. The valve 84 includes cone 86 and valve block 88. The cone 86 is sealed against seat 90 when the valve system is in the second closed position or the pumping position. The pump 24 in FIG. 12 is in fluid communication with reservoir 14 (not shown) through valve 62, passageway 92 and tube 16 (not shown). The pump 24 is in fluid communication with tubular chamber 18 (partly shown) through high pressure check valve 60 and fluid channel 94, as shown in FIGS. 13 and 14.

The low pressure valve 62 communicates at its proximal end with a radially oriented passageway 96 which in turn communicates with a transverse, radially oriented passageway 98 which is generally perpendicular to passageway 96. The passageway 96 communicates with the axial, lengthwise passageway 92. The passageway or conduit 92 extends from the distal section 20 to the proximal section 22 in fluid isolation from the tubular chamber 18.

The tubular chamber 18 has three layers 36, 38 and 40 which are as described with reference to FIGS. 3 and 4.

OPERATION

Tubular chamber 18, pump 24, and fluid reservoir 14 are supplied with biocompatable fluid by means known to those of skill in the art. Prosthesis 10 is then implanted by surgical means known in the art. Once implanted, when an erection of the penis is to be produced, the user squeezes distal section 20. On repeated squeezing and releasing of the distal section, fluid fills tubular chamber 18 substantially to capacity and the desired stiffness and girth of tubular body 12, and the penis, is attained.

Referring to FIGS. 3 and 4, on squeezing distal section 20, fluid transfers from pump 24 through first passageway 32 to pressure valve 28. Valve 28 opens due to the fluid pressure and fluid enters tubular chamber 18. The user then releases distal section 20, creating a vacuum in first passageway 32, so opening suction valve 30, and drawing fluid from fluid reservoir 14 through reservoir tube 16 and transfer passage 58 into pump 24.

The user deflates the prosthesis 10 by laterally squeezing tubular body 12 at the location of ball deflate valve 26. The squeezing action deforms housing 42 of valve 26 and allows fluid from tubular chamber 18 past ball 48 through second passageway 34, transfer passage 58, and reservoir tube 16 to return to fluid reservoir 14 until the penis is flaccid. The direction of the fluid is indicated by arrows in FIG. 3.

Referring to FIGS. 6 to 8, on squeezing distal section 20, fluid transfers from pump 24 through high pressure check valve 60 to tubular chamber 18, as shown by broken arrows (→) in FIG. 7. The user then releases distal section 20, creating a low pressure in pump 24 so opening low pressure check valve 62, and drawing fluid from fluid reservoir 14 through central lumen 66, bend valve 64 and valve 62 into pump 24, as indicated by solid arrows (→) in FIG. 7. The user deflates the prosthesis 10 by bending the penis such that bend valve 64 is at an angle relative to valve block 68. The bending action forces the fluid under pressure in tubular chamber 18 to pass between valve block 68 and bend valve 64 through central lumen 66 and tube 16 to the fluid reservoir until the penis is flaccid. The arrows in FIG. 8 show the flow of the fluid during the bending.

Referring to FIGS. 9 to 11, on squeezing distal section 20, fluid transfers from pump 24 through flap valve 70 into tubular chamber 18, as indicated by arrows in FIG. 9. The user then releases distal section 20 creating a low pressure in pump 24 so opening poppet valve 72 and closing flap valve 70, and drawing fluid from the fluid reservoir 14 through lumen 66 into pump 24, as indicated by arrows in FIG. 10. The user deflates the prosthesis 10 by supporting the penis at a position proximal to double flange valve 74 and by bending distal section 20 such that spring retainers 80 are in a flexed position, and valve 74 opens. The user's action forces the fluid under pressure in tubular chamber 18 to pass through open valve 74 and lumen 66 to the reservoir 14 until the penis is flaccid. The arrows in FIG. 11 indicate the flow of fluid during the bending action.

Referring to release valve 84 of FIGS. 12 to 14 in conjunction with FIGS. 3, 4 and 5 as suggested above, on squeezing distal section 20, fluid transfers from pump 24 through first passageway 32 to pressure valve 28. Due to the fluid pressure, valve 28 opens and fluid enters tubular chamber 18. The user then releases distal section 20, creating a vacuum in first passageway 32, so opening suction valve 30, and drawing fluid from fluid reservoir 14 through reservoir tube 16 and transfer passage 58 into tubular chamber 18.

The user deflates the prosthesis 10 by laterally squeezing tubular body 12 at the valve block 88, as in FIG. 14, or by bending the penis at valve stem 87 as shown in FIG. 13. The squeezing or the bending deforms valve block 88 and allows fluid from tubular chamber 18 past cone 86 through second passageway 34, transfer passage 58, and reservoir tube 16 to fluid reservoir 14 (not shown) until the penis is flaccid. The directions of the fluids are indicated by arrows in FIGS. 12 to 14.

Referring to FIGS. 12 to 14 in conjunction with FIG. 6, on squeezing distal section 20, fluid transfers from pump 24 through high pressure check valve 60 and fluid channel 94 to tubular chamber 18, as indicated by broken arrows in FIG. 12. High pressure check valve 60 opens due to the fluid pressure exerted by the squeezing action. The user then releases distal section 20, creating a low pressure in pump 24 so opening low pressure check valve 62, and drawing fluid from fluid reservoir 14 through passageway 92 into pump 24 as indicated by solid arrows in FIG. 12.

The user deflates the prosthesis 10 by laterally squeezing tubular body 12 at the valve block 88, as in FIG. 14, or by bending tubular body 12 at cone 86, as shown in FIG. 13. The squeezing or bending deforms valve block 88 and allows fluid to flow from tubular chamber 18 past cone 86 through passageways 96 and 92 and tube 16 to fluid reservoir 14. Alternatively or simultaneously, fluid flows from tubular chamber 18 past cone 86 through passageway 98 between outer layer 36 and middle layer 38 to passageway 92. On removal of squeeze or bend forces on the valve block, the seat 90 returns to its original shape, and the cone 86 creates a seal with the valve block 88.

The invention has been described with respect to four embodiments. Those skilled in the art will appreciate variations and modifications thereof. The following claims are intended to cover all modifications and variations falling within the spirit and scope of the invention.

We claim:

1. An implantable penile prostheses comprising:
   1) a generally tubular body implantable within one or each of the corpus cavernosa of the penis to simulate a natural erection; and
   2) a fluid reservoir implantable in a patient's body in fluid communication with said tubular body;
   said tubular body comprising:
   a generally tubular chamber inflatable from a flaccid to an erect state when filled with a fluid substantially to capacity and deflatable from the erect state to the flaccid state when substantially free of fluid, said tubular chamber being in fluid communication with said fluid reservoir through a second passageway which is defined by a conduit extending axially along the length of said tubular body externally of said tubular chamber;
   a manually actuatable valve system for controlling fluid flow between said tubular chamber and said fluid reservoir; and
   a proximal section and a distal section;
   said valve system comprising a first valve for controlling fluid flow from said tubular chamber to said fluid reservoir to attain the flaccid state, and a pump and a second valve to allow an irreversible fluid flow from said fluid reservoir to said tubular chamber to attain the erect state on compressing said pump, said pump located in said distal section and said second valve located in said proximal section, both of said pump and said second valve being in series with said tubular chamber along the length of said tubular body, said pump and said second valve being in fluid communication through a first passageway which is in fluid isolation from said second passageway defined by a conduit extending axially along the length of said tubular body externally of said tubular chamber.

2. A prosthesis according to claim 1 wherein said tubular chamber is defined by a body made of a limited distensible material.

3. An implantable penile prosthesis comprising:
   1) a generally tubular body implantable within one or each of the corpus cavernosa of the penis to simulate a natural erection; and
   2) a fluid reservoir implantable in a patient's body in fluid communication with said tubular body;
   said tubular body comprising:
   a) a generally tubular chamber inflatable from a flaccid to an erect state when filled with a fluid substantially to capacity and deflatable from the erect state to the flaccid state when substantially free of fluid; and
   b) a manually actuatable valve system for controlling fluid flow between said tubular chamber and said fluid reservoir, said valve system movable between a first open position allowing for change from the erect state to the flaccid state, and a second closed position allowing for change from the flaccid state to the erect state, by bending of the penis.

4. A prosthesis according to claim 3 wherein said tubular chamber is defined by a body made of a limited distensible material.

5. A prosthesis according to claim 3 wherein said tubular body has a proximal section and a distal section, and said valve system is located in said distal section.

6. A prosthesis according to claim 5 wherein said valve system is in fluid communication with said reservoir through a lumen which is defined by a conduit extending axially along the length of said tubular body from said valve system to said proximal section.

7. A prosthesis according to claim 6 wherein said lumen is located internally of said tubular body.

* * * * *